United States Patent
Lawton et al.

(10) Patent No.: US 9,309,114 B2
(45) Date of Patent: Apr. 12, 2016

(54) POROUS NANOPARTICLES PRODUCED BY SOLVENT-FREE EMULSIFICATION

(71) Applicant: XEROX CORPORATION, Norwalk, CT (US)

(72) Inventors: David John William Lawton, Stoney Creek (CA); Santiago Faucher, Oakville (CA)

(73) Assignee: XEROX CORPORATION, Norwalk, CT (US)

(*) Notice: Subject to any disclaimer, the term of this patent is extended or adjusted under 35 U.S.C. 154(b) by 51 days.

(21) Appl. No.: 13/740,314

(22) Filed: Jan. 14, 2013

(65) Prior Publication Data
US 2014/0199352 A1  Jul. 17, 2014

(51) Int. Cl.
| B01J 13/00 | (2006.01) |
| B82Y 40/00 | (2011.01) |
| A61K 8/11 | (2006.01) |
| A61K 9/51 | (2006.01) |

(52) U.S. Cl.
CPC . B82Y 40/00 (2013.01); A61K 8/11 (2013.01); A61K 9/51 (2013.01); B01J 13/0091 (2013.01); *Y10T 428/2982* (2015.01); *Y10T 428/2998* (2015.01)

(58) Field of Classification Search
None
See application file for complete search history.

(56) References Cited

U.S. PATENT DOCUMENTS

| 4,594,390 | A * | 6/1986 | Abdou-Sabet et al. | ....... 525/232 |
| 6,063,827 | A | 5/2000 | Sacripante et al. | |
| 6,593,049 | B1 | 7/2003 | Veregin et al. | |
| 6,756,176 | B2 | 6/2004 | Stegamat et al. | |
| 6,830,860 | B2 | 12/2004 | Sacripante et al. | |
| 2006/0222991 | A1 | 10/2006 | Sacripante et al. | |
| 2006/0223934 | A1 * | 10/2006 | Chen et al. | ..................... 524/500 |
| 2010/0216804 | A1 * | 8/2010 | Zale et al. | ..................... 514/249 |
| 2011/0020648 | A1 * | 1/2011 | Fukazawa et al. | ........ 428/402.22 |
| 2011/0150985 | A1 * | 6/2011 | Blair et al. | ..................... 424/451 |
| 2012/0003581 | A1 * | 1/2012 | Yang et al. | ............... 430/137.14 |

FOREIGN PATENT DOCUMENTS

WO   WO 2009103680 A1 *   8/2009

OTHER PUBLICATIONS

Akay (G. Akay & L. Tong, Preparation of Colloidal Low-Density Polyethylene Latexes by Flow-Induced Phase Inversion Emulsification of Polymer Melt in Water, 239 J. Colloid Interface Sci., pp. 342-357 (2001)).*
English Language Translation of WO 2009/103680 A1.*

* cited by examiner

*Primary Examiner* — Bethany Barham
*Assistant Examiner* — Dominic Lazaro
(74) *Attorney, Agent, or Firm* — Pillsbury Winthrop Shaw Pittman LLP

(57) ABSTRACT

The process for manufacturing porous nanoparticles disclosed herein includes feeding a dry-blended mixture of at least one resin and a neutralizing agent into a feed section of a screw extruder, injecting a surfactant solution downstream of the hopper, and adding an aqueous composition both directly after the surfactant solution as well as further downstream. Porous nanoparticles having a particle size of from about 50 nm to about 2 μm and a pore diameter of from about 20 nm to about 400 nm may be continuously recovered from the extruder following this process.

9 Claims, 5 Drawing Sheets

POROUS NANOPARTICLES PRODUCED BY SOLVENT-FREE EMULSIFICATION

TECHNICAL FIELD

The present disclosure relates to porous nanoparticles and methods of producing the porous nanoparticles.

BACKGROUND

Materials of high surface area and porosity have found great utility in a range of industries including, for example, the automotive, cosmetic, coatings, and chemical industries. For instance, in the automotive industry, porous materials are currently being researched to lighten car parts, reduce material costs, and improve fuel efficiency. In the cosmetic industry, porous particles may be used as delivery vehicles for oils and other cosmetics, allowing these materials to be handled as a powder rather than a paste. In the coatings industry, porous materials or films may be used to reduce the amount of resin used in covering a surface, or such materials may be used in producing a paint that is porous (breathable) for moisture transmission and control. In the chemical industry, nanoporous materials may be used for gas adsorption, filtration and chromatography.

Various methods have been developed for the production of porous materials of small size. However, few approaches have been developed for the production of porous nanosize particles from polymeric materials. One conventional process involves producing core shell particles, but the approaches used to produce these hollow micron-sized spheres are not practical on a large scale and make use of complicated phase inversion chemistries, step-by-step assemblies, or microfluidics.

A new mechanism or chemistry that would produce porous nanoparticles by a simplified manufacturing process would therefore be desirable.

SUMMARY

Disclosed herein is a process for manufacturing porous nanoparticles. In some embodiments, the process includes adding a first aqueous solution containing a surfactant to a resin composition containing at least one resin to form a water-in-oil emulsion. A second aqueous solution containing deionized water may be added to the water-in-oil emulsion prior to phase inversion to form a water-in-oil-in-water double emulsion comprising porous nanoparticles, and porous nanoparticles may be recovered from the double emulsion. The porous nanoparticles may have a particle size of from about 50 nm to about 2 μm and a pore diameter of from about 20 nm to about 400 nm.

Also provided is a continuous process for producing porous nanoparticles which, in some embodiments, involves continuously adding a resin composition comprising at least one resin to a feed section of the screw extruder. A first aqueous solution containing a surfactant may be added to the resin composition to form a water-in-oil emulsion, and a second aqueous solution containing deionized water may be added to the water-in-oil emulsion prior to phase inversion to form a water-in-oil-in-water double emulsion comprising porous nanoparticles. In embodiments, porous nanoparticles may be recovered from the double emulsion.

Further provided are porous nanoparticles containing at least one polyester resin in the absence of an organic solvent, and a surfactant. The porous nanoparticles may have a particle size of from about 50 nm to about 2 μm and a pore diameter of from about 20 nm to about 400 nm.

EMBODIMENTS

Figure 1:
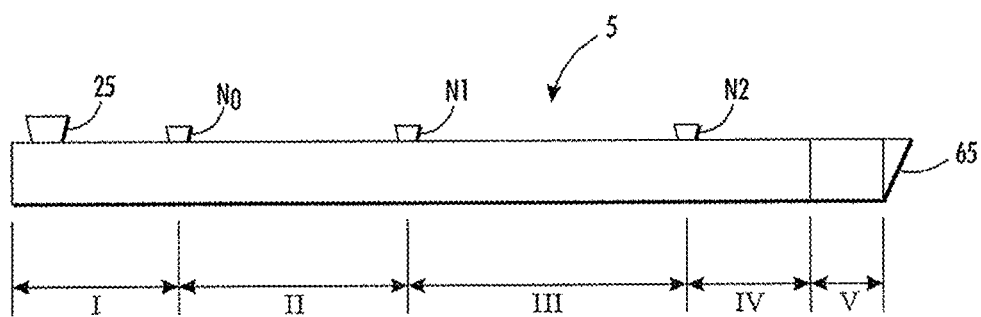
FIG. 1 is a cross-sectional view of an exemplary screw extrusion device that may be employed in the processes of the present disclosure.

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. All ranges disclosed herein include, unless specifically indicated, all endpoints and intermediate values.

As used herein, the modifier, "about," used in connection with a quantity is inclusive of the stated value and has the meaning dictated by the context (for example, it includes at least the degree of error associated with the measurement of the particular quantity). When used in the context of a range, the modifier, "about," should also be considered as disclosing the range defined by the absolute values of the two endpoints. For example, the range, "from about 2 to about 4," also discloses the range, "from 2 to 4."

The present disclosure provides processes for forming porous nanoparticles, such processes for forming porous nanoparticles in the absence of an organic solvent. In embodiments, a process of the present disclosure includes utilizing an extruder, such as a twin-screw extruder, to carry out continuous phase inversion of a continuous polymer phase into a flowable latex emulsion.

The term "emulsion" refers, for example, to a mixture of two or more liquids in which one liquid ("dispersed phase") is dispersed in a second ("continuous phase"). The phrase "continuous phase inversion" refers, for example, to a situation in which a substance initially comprising the continuous phase inverts to become the dispersed phase, and vice versa.

In embodiments, the processes for forming porous nanoparticles of the present disclosure may occur in the "absence of an organic solvent." The phrase in the "absence of an organic solvent" refers, for example, to a process in which the solutions and/or compositions utilized in the process are substantially free of organic solvents or free of organic solvents. The phrase "substantially free of organic solvents" refers, for example, to a composition or solution where there are only minor amounts of organic solvents present and/or only a minor amount of organic solvent has not been removed; such as, for example, less than about 2% by weight organic solvent is present in any composition and/or solution utilized in the process, or from about 1% to about 0.001% by weight organic solvent is present in any composition and/or solution utilized in the process. The term "free of organic solvents" refers, for example, to a composition or solution where there are no organic solvents are present and/or all organic solvents have been removed from the composition or solution. In specific embodiments, each of the compositions and/or solutions used and/or added during the process of forming the porous nanoparticles of the present disclosures are either free or substantially free of organic solvents.

For example, in embodiments, organic solvents may not be used to dissolve the polyester resin for emulsification. However, minor amounts of organic solvents may be present in such resins as a consequence of their use in the production process of forming the polyester resin, but such solvents are not present in a sufficient amount to dissolve the polyester resin for emulsification. The term "minor" refers, for example, to trace amounts of organic solvents in the resin, such as, for example, less than about 1% organic solvents, such as from about 1% to about 0.001% organic solvents by weight relative to the total weight of the resin. In embodiments, amounts of organic solvents in the resin may be less than about 0.1% organic solvents by weight relative to the total weight of the resin.

In the methods of the present disclosure, continuous phase inversion of a continuous polymer phase into a flowable latex emulsion may be carried out with an extruder, such as a twin-screw extruder. In embodiments, forming porous nanoparticles in the absence of an organic solvent by continuous phase inversion of a continuous polymer phase into a flowable latex emulsion may completely occur within the confines of one extruder, such as a twin-screw extruder. The porous nanoparticles formed in the absence of an organic solvent by the continuous phase inversion process of the present disclosure may be used to produce porous nanoparticles having nanopores, such as nanopores having a diameter of less than about 400 nm, such as pores having a diameter in the range of from about 20 nm to about 400 nm, or from about 25 nm to about 180 nm, or pores having a diameter in the range of from about 30 nm to about 100 nm, or pores having a diameter in the range of from about 40 nm to about 80 nm. Such nanopores may have an average diameter in the range of from about 40 nm to about 100 nm, or about 50 nm to about 70 nm. In embodiments, the porous nanoparticles formed in the absence of an organic solvent by the continuous phase inversion process of the present disclosure may be used to produce porous nanoparticles having cell walls with a cell wall thickness in the range of from about 5 nm to about 100 nm, such as a cell wall thickness in the range of from about 10 nm to about 50 nm, or a cell wall thickness in the range of from about 15 nm to about 30 nm, or cell walls having an average cell wall thickness of from about 18 nm to about 22 nm, or of about 20 nm.

The methods of the present disclosure may include the addition of a resin, such as polyester, or an amorphous polyester, blended with a basic powder, such as NaOH powder, to the hopper of an extruder, such as a twin-screw extruder, by any suitable means, such as a gravimetric feeder. The methods may also include adding surfactant solution to the resin. The surfactant solution may be added to the hopper with the resin, or it may be added at a section of the extruder downstream of the hopper. Additionally, deionized water may be added at multiple locations along the extruder, such as both directly after the surfactant solution as well as further downstream. In embodiments, deionized water may also be added outside of the screw extruder.

The average residence time within the extruder may be tailored as desired in order to achieve the desired porous nanoparticle size. The term "residence time" refers, for example, to the time that elapses in the process from feeding the resin component to the extruder to the porous nanoparticles exiting the extruder. In embodiments, the average residence time within the extruder may be in the range of from about 1 minute to about 2 hours, such as in the range of from about 2 minutes to about 30 minutes, or in the range of from about 4 minutes to about 10 minutes.

The nanoporous latex emulsion produced according to the processes of the present disclosure may have a particle size of from about 50 nm to about 2 µm, such as from about 75 nm to about 1 µm, or from about 100 nm to about 500 nm.

Continuous Process

In embodiments, the present disclosure provides a continuous process for manufacturing porous nanoparticles. The term "continuous" refers, for example, to a process that may be performed without interruption, that is, a process in which raw materials are continuously processed to completed products. While a continuous process may thus be conducted 24 hours per day, 7 days per week, it is understood that the process may be periodically stopped, such as for maintenance purposes.

Embodiments of the continuous process for producing porous nanoparticles disclosed herein may include continuously feeding components into a feed section of a screw extruder. In embodiments, the process may comprise dry-blending at least one resin and a neutralizing agent in the absence of a solvent to form a resin mixture. The term "dry-blending" refers, for example, to a mixing process (typically, a low-shear mixing process) in which ingredients are blended together to form a relatively free-flowing heterogeneous mixture of the ingredients in particulate form. The neutralizing agent may be present in a concentration of from about 0.1 ppH (parts per hundred) to about 3 ppH, such as from about 0.3 to about 2 ppH, or from about 0.25 to about 1.0 ppH. Concentration of the components is provided rather than the rates to achieve the desired composition, since flow and feed rates vary with the scale of the processing equipment.

In embodiments, a first aqueous solution comprising a surfactant may be added to the resin mixture in the extruder. The first aqueous solution comprising a surfactant may be co-fed with the resin into the extruder feed hopper, or the first aqueous solution may be added to the resin mixture in the extruder at a location along the extruder downstream from the feed section. The first aqueous solution comprising a surfactant may be fed at a rate such that the surfactant is at a concentration of from about 2% by weight to about 15% by weight of the resin, such as from about 2.5% by weight to about 10% by weight of the resin, or from about 3% by weight to about 8% by weight of the resin.

In embodiments, the neutralizing agent may be co-fed with the first aqueous solution comprising surfactant. For example, in embodiments, a dry-blended resin composition may be added at the feed section of the extruder, and then the neutralizing agent and the first aqueous solution comprising a surfactant may be co-fed at a section of the extruder downstream from the feed section.

In embodiments, the first aqueous solution comprising a surfactant may further contain at least one active compound or material, such as a cosmetic, a chemical and/or a pharmaceutical. The term "active compound" refers for example to an agent, drug, compound, composition of matter or mixture thereof which provides some chemical, physiological, psychological, biological, or pharmacological, and often beneficial, effect when in the environment of use.

Suitable active compounds may include foods, food supplements, nutrients, drugs, antacids, vitamins, antibacterial agents, antifungal agents, antibiotics, anti-inflammatory agents, other compounds that provide a benefit in the environment of use. For example, active compounds may include any physiologically or pharmacologically active substance that produces a localized or systemic effect or effects in animals, such as mammals, for example, humans. Active compounds may also include any desired inorganic and organic compounds.

In embodiments, the active compounds may be selected from, for example, proteins, enzymes, enzyme inhibitors, hormones, polynucleotides, nucleoproteins, polysaccharides, glycoproteins, lipoproteins, polypeptides, steroids, hypnotics and sedatives, psychic energizers, tranquilizers, anticonvulsants, antidepressants, muscle relaxants, antiparkinson agents, analgesics, anti-inflammatories, antihistamines, local anesthetics, muscle contractants, antimicrobials, antimalarials, antivirals, antibiotics, antiobesity agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

The at least one active compound or material may be present in any effective amount. In embodiments, the amount of active compounds present in the porous particle may be tuned as desired, for example by varying the amount and/or timing of the addition of the active compound to arrive at the desired active compound content.

In embodiments, the active compound may be added at the same time (and optionally mixed with) the surfactant solution. The amounts of active compounds in the surfactant solution may vary depending on the desired effect and/or the desired amount of active compound to be included in the porous particle. In embodiments where the at least one active compound is added at the same time (and optionally mixed with) the surfactant solution, the at least one active compound or material and the surfactant may together comprise, for example, less than about 50 percent by weight of the first aqueous solution, such as from about 10 to about 45 percent by weight of the first aqueous solution, or from about 20 to about 40 percent by weight of the first aqueous solution. For example, in embodiments, the at least one active compound may comprise from about 1 to about 40 percent by weight of the first aqueous solution, such as from about 5 to about 30 percent by weight, or from about 10 to about 25 percent by weight of the first aqueous solution.

The addition of the first aqueous solution comprising a surfactant to the resin composition may facilitate the production of a water-in-oil emulsion. That is to say, the surfactant solution may become emulsified and dispersed within the resin (continuous phase), forming a water-in-oil emulsion of the surfactant solution within the resin. In embodiments, a second aqueous solution comprising deionized water may be added to the emulsion at a location further downstream from the location where the first aqueous solution comprising a surfactant is added. The second aqueous solution comprising deionized water may be added before phase inversion of the emulsion; for example, in embodiments, the second aqueous solution comprising deionized water may be added directly after the first aqueous solution comprising a surfactant. Addition of the second aqueous solution comprising deionized water may be achieved via water injection ports into the extruder.

In embodiments, the second aqueous solution may further comprise a surfactant. Including a surfactant in the second aqueous solution comprising deionized water may be used to promote pore formation at the surface of the porous nanoparticles. For example, injecting a second aqueous solution comprising deionized water and surfactant may, in embodiments, produce porous nanoparticles with an increased degree of surface porosity (as compared to internal porosity), such as a surface porosity of from about 10% to 60% of the surface of the nanoparticles, or from about 20% to about 50%, or from about 30% to about 40%. Surface porosity may also be increased by increasing the injection rate of the second aqueous solution comprising deionized water (not necessarily comprising surfactant).

Phase inversion may occur following the addition of deionized water to the water-in-oil emulsion of the resin mixture and surfactant, yielding a double emulsion (that is, a water-in-oil-in-water emulsion) comprising porous nanoparticles. For example, deionized water may be added to form a double emulsion with a solids content (by weight) of from about 5% to about 75%, such as from about 10% to about 50%, or from about 20% to about 40%. The term "double emulsion" refers, for example, to a colloid in which a first emulsion is dispersed within another liquid. The other liquid may be a third liquid, or a second instance of the inner liquid of the first emulsion.

In embodiments, deionized water may be added at a second location downstream from the first deionized water addition location and/or after the double emulsion is collected from the extruder. For example, the extruder may discharge the emulsion into a stirred reactor, where deionized water may be added. Deionized water may be added in any effective amount to dilute the double emulsion comprising porous nanoparticles and increase flowability of the double emulsion.

The extruder may have segmented barrels and the temperature, as well as other process parameters, of each barrel section may be controlled independently. For example, the heating and cooling of each barrel may be controlled independently. The screw elements of the extruder may be segmented for ease of design and to meet particular mixing dynamics at different sections for particular reactions and proper dispersions, such as neutralization reactions, water-in-oil dispersions, stabilization, and phase inversion to produce porous nanoparticles having a desired particle size and pore size, such as nano-sized particles with nanoporous features. The process disclosed herein may be used to produce fully-formed porous nanoparticles with desired particle sizes that may be collected from the extruder. As used herein, "fully formed" indicates that there are discrete polymer particles within a continuous aqueous medium.

In embodiments, extrusion conditions such as temperature, screw speed, feed rate of mixture components may be adjusted to facilitate production of porous nanoparticles. For instance, the screw speed varies depending on the size of the extruder and may be at a rate of from about 50 rpm to about 600 rpm, such as from about 100 rpm to about 500 rpm, or from about 200 rpm to about 300 rpm. For example, for an 18 mm extruder, the screw speed may be from about 100 rpm to about 300 rpm. In embodiments, the temperature of each barrel may be from about 70° C. to about 200° C., such as from about 80° C. to about 180° C., or from about 85° C. to about 175° C. In embodiments, the temperature of each barrel may vary depending on the zone within the extruder. For example, within a melting zone, the temperature may be from about 65° C. to about 200° C., such as from about 75° C. to about 190° C., or from about 85° C. to about 175° C., and within a dispersion zone, the temperature may be from about 50° C. to about 150° C., such as from about 70° C. to about 140° C., or from about 80° C. to about 130° C.

The length/diameter (L/D) ratio of the extruder may be lengthened or shortened. In addition, mixing intensity, shear stress, and shear rate may be adjusted by proper screw design to meet desired mixing dynamics for particular processes. For example, the mixing may be distributive, dispersive, dissipative, and/or chaotic. Fill volumes, local pressure, and feed rate, for example, may be controlled by varying screw speeds.

The time the components stay in the extruder may be lengthened or shortened to produce porous nanoparticles having a desired particle size and pore size. For example, in embodiments, the average residence time within the extruder may be in the range of from about 1 minute to about 2 hours, such as in the range of from about 2 minutes to about 30 minutes, or in the range of from about 4 minutes to about 10 minutes. When the extruder has segmented elements, the time the components stay in one segment may be lengthened or shortened.

In embodiments, the porous nanoparticles may be recovered from the water-in-oil-in-water double emulsion. In embodiments, porous nanoparticles may be recovered from the double emulsion when it is discharged from the screw extruder. Consequently, the above steps produce porous particles with desired particle size and pore size, such as nano-sized particles with nanoporous features.

In embodiments, the pores of the porous nanoparticles produced according to the instant disclosure may be loaded with a material apart from the resin matter. For example, the pores of the porous nanoparticles may be partially or completely filled or loaded with an active compound or material, such as a cosmetic, a chemical and/or a pharmaceutical. In embodiments, such loaded particles may comprise at least one active compound, such as a cosmetically or pharmaceutically active compound, where the at least one active compound is present inside the particles. Such active compounds may also be present at the surface of loaded particles.

Particles may be loaded with an active material by any suitable means. For example, as discussed above, the particles may be loaded with an active material by feeding an active compound to the extruder with the first aqueous solution comprising a surfactant. The active compound may also be added to the surface of the loaded particles. In embodiments, the ratio by weight of the at least one cosmetically or pharmaceutically active compound to the weight of the porous particles may be from about 1:1000 to about 10:1, such as about 1:100 to about 1:1.

Amounts of active compounds introduced into particles may depend on the desired effect. In embodiments, the active compound or material, such as a cosmetic, a chemical and/or a pharmaceutical, may be present in the porous particles in an amount of active material ranging from about 1 to 43% by weight, such as from about 2 to about 40% by weight, or from about 5 to about 30% by weight, relative to the total weight of the particles once loaded.

FIG. 1 is a cross-section schematic diagram of an embodiment of a continuous process for manufacturing porous nanoparticles. Embodiments of the process use a screw extruder 5, shown as a multi-screw extruder, to which the resin and neutralizing agent mixture may be fed. A twin-screw extruder may be used in various applications. For example, a twin screw extruder may provide types of mixing such as distributive mixing, dispersive mixing, dissipative mixing, chaotic mixing, and pumping. A twin screw extruder allows the resin and neutralizing agent to be co-fed into the twin screw extruder at a defined rate, to add a surfactant solution in a downstream portion of the extruder, to add a first and second aqueous solution at further downstream portions of the extruder, and to emulsify the components in the extruder.

In FIG. 1, a dry-blended resin mixture of a resin and a neutralizing agent may be fed into the screw extruder 5 at a controlled rate through a hopper 25 by means of a gravimetric feeder (not shown). After being fed into the screw extruder 5, the resin mixture passes through a feed section I of the extruder 5. A first aqueous solution comprising a surfactant may be added through injection port $N_0$, forming a water-in-oil emulsion with the resin solution as it passes through section II of the extruder 5. A second aqueous solution comprising deionized water may be added through injection port N1, before the emulsion undergoes phase inversion, yielding a water-in-oil-in-water double emulsion with nanoporous morphology as the emulsion passes through section III of the extruder 5. Deionized water may be added through an injection port N3, to dilute the water-in-oil-in-water double emulsion and make it more freely flowing. The latex emulsion with nanoporous morphology having a desired particle size and a desired pore size emerges at the end 65 of the extruder 5 and may be analyzed for uniformity, pore size, and particle size.

The extruder 5 comprises a screw shaft that may be connected to a motor (not shown) through a gear box (not shown) to turn the screw. The screw speed may be accurately controlled by the motor and the gear box. A barrel (not shown) provides a housing for the screws. Both the barrel and the screw may be segmented and each section may be heated at a desired temperature. Because the screw extruder 5 may be segmented and the temperature of each section may be controlled independently at a desired temperature. For example, the multiple segments may each be heated to a temperature of from about 70° C. to about 200° C., such as from about 80° C. to about 180° C., or from about 85° C. to about 175° C. In embodiments, the segments may be heated to form a temperature gradient. The ability to set different temperature profiles along the barrel may allow for greater control of particle size and uniformity.

As discussed above, the resin and the neutralizing agent may be added to the extruder through a hopper 25 in the feed section I of the extruder 5. Prior to the feeding, the toner components may be dry-blended for a period of from about 5 minutes to about 60 minutes, such as from about 10 minutes to about 50 minutes, or from about 15 minutes to about 45 minutes. Alternatively, the resin and neutralizing agent may be co-fed independently using separate gravimetric feeders, as the components will become well-mixed in the melting/metering region of the extruder.

A first aqueous solution comprising a surfactant and optionally an active agent may be added at injection port $N_0$. The injection port $N_0$ may be located downstream of a melting/metering region and upstream of a dispersion region. To produce sufficient shearing to occur at the barrel-wall of the extruder, the extruder may be fully filled in the injection region. Local pressures may be dependent on the amount of water added, the temperature of the barrel, and the amount of surfactant used. In embodiments, the pressure may be from about 100 to about 1000 psi. The feeding rate for an 18 mm extruder with 40 L/d may be from about 0.5 kg/hr to about 2.5 kg/hr. In embodiments, the screw speed may be from about 100-600 RPM. In embodiments, the surfactant solution may be pre-heated, such as to match the barrel temperature.

While FIG. 1 indicates that the resin and neutralizing agent are added through the hopper 25 and the surfactant (and optionally active agent) are added through the injection port $N_0$, the neutralizing agent may be co-fed with the surfactant (and optionally an active agent) at other locations, such as at injection port $N_0$, or the resin, the neutralizing agent, and the surfactant (optionally with an active agent) may be co-fed through the hopper 25.

In embodiments, the first aqueous solution comprising a surfactant (and optionally an active agent) may be mixed with the resin and neutralizing agent in the section II of the extruder 5, such that a water-in-oil emulsion is formed. Prior to phase inversion of the emulsion in section III of the extruder 5, deionized water may be added through injection port N1. For example, in embodiments, injection port N1 may be located directly adjacent to injection port $N_0$ (if the first aqueous solution comprising surfactant is added through injection port $N_0$) or directly adjacent to the hopper 25 (if the surfactant is added through the hopper 25). In embodiments, the deionized water may be pre-heated, such as to the barrel temperature, prior to injection to minimize temperature drop within the barrel of the extruder. A water-in-oil-in-water double emulsion may be produced as the mixture passes through section III of the extruder 5.

The mixture may then be continuously fed to a section IV of the extruder 5, where deionized water may optionally be added through injection port $N_2$ to dilute the double emulsion and make it more flowable. The deionized water may be pre-heated, for example to the barrel temperature, prior to injection to minimize temperature drop within the barrel of the extruder. In other embodiments, deionized water is not added to the extruder after the formation of the double emulsion, and the undiluted double emulsion may proceed directly to the pumping zone V of the extruder for collection.

The double emulsion may then be pumped through the pumping zone V of the extruder 5 and collected from the end of the extruder, and porous nanoparticles may be continuously collected. In embodiments, the average residence time within the extruder may be in the range of from about 1 minute to about 2 hours, such as in the range of from about 2 minutes to about 30 minutes, or in the range of from about 4 minutes to about 10 minutes.

If a second deionized water injection is not added in the extruder to dilute the solution and make it more flowable, or if further dilution of the double emulsion is desired, the double emulsion may be collected, for example in a continuous stirred-tank reactor, and deionized water may be added outside of the extruder. Porous nanoparticles may then be collected.

Resins

Any suitable resin may be utilized in the processes of the present disclosure. In embodiments, the resins may be an amorphous resin, a crystalline resin, and/or a combination thereof. In further embodiments, the resin may be a polyester resin, including the resins described in U.S. Pat. Nos. 6,593, 049 and 6,756,176, the disclosures of each of which are hereby incorporated by reference in their entireties. Suitable resins may also include a mixture of an amorphous polyester resin and a crystalline polyester resin as described in U.S. Pat. No. 6,830,860, the disclosure of which is hereby incorporated by reference in its entirety.

In embodiments, the resin may be a polyester resin formed by reacting a dial with a diacid in the presence of an optional catalyst. For forming a crystalline polyester, suitable organic dials include aliphatic dials with from about 2 to about 36 carbon atoms, such as 1,2-ethanediol, 1,3-propanediol, 1,4-butanediol, 1,5-pentanedial, 2,2-dimethylpropane-1,3-diol, 1,6-hexanediol, 1,7-heptanediol, 1,8-octanediol, 1,9-nonanediol, 1,10-decanediol, 1,12-dodecanediol and the like including their structural isomers. The aliphatic diol may be, for example, selected in an amount of from about 40 to about 60 mol %, such as from about 42 to about 55 mol %, or from about 45 to about 53 mol %, and a second diol can be selected in an amount of, for example, from about 0 to about 10 mol %, such as from about 1 to about 4 mol % of the resin.

Examples of organic diacids or diesters including vinyl diacids or vinyl diesters selected for the preparation of the crystalline resins include oxalic acid, succinic acid, glutaric acid, adipic acid, suberic acid, azelaic acid, sebacic acid, fumaric acid, dimethyl fumarate, dimethyl itaconate, cis, 1,4-diacetoxy-2-butene, diethyl fumarate, diethyl maleate, phthalic acid, isophthalic acid, terephthalic acid, naphthalene-2,6-dicarboxylic acid, naphthalene-2,7-dicarboxylic acid, cyclohexane dicarboxylic acid, malonic acid and mesaconic acid, a diester or anhydride thereof. The organic diacid may be selected in an amount of, for example, from about 40 to about 60 mol %, such as from about 42 to about 52 mol %, or from about 45 to about 50 mol %, and a second diacid can be selected in an amount of from about 0 to about 10 mol % of the resin, such as from about 1 to about 9 mol % of the resin, or from about 2 to about 8 mol % of the resin.

Examples of crystalline resins include polyesters, polyamides, polyimides, polyolefins, polyethylene, polybutylene, polyisobutyrate, ethylene-propylene copolymers, ethylene-vinyl acetate copolymers, polypropylene, mixtures thereof, and the like. Specific crystalline resins may be polyester based, such as poly(ethylene-adipate), poly(propylene-adipate), poly(butylene-adipate), poly(pentylene-adipate), poly(hexylene-adipate), poly(octylene-adipate), poly(ethylene-succinate), poly(propylene-succinate), poly(butylene-succinate), poly(pentylene-succinate), poly(hexylene-succinate), poly(octylene-succinate), poly(ethylene-sebacate), poly(propylene-sebacate), poly(butylene-sebacate), poly(pentylene-sebacate), poly(hexylene-sebacate), poly(octylene-sebacate), poly(decylene-sebacate), poly(decylene-decanoate), poly(ethylene-decanoate), poly(ethylene dodecanoate), poly(nonylene-sebacate), poly(nonylene-decanoate), copoly(ethylene-fumarate)-copoly(ethylene-sebacate), copoly(ethylene-fumarate)-copoly(ethylene-decanoate), copoly(ethylene-fumarate)-copoly(ethylene-dodecanoate), copoly(2,2-dimethylpropane-1,3-diol-decanoate)-copoly(nonylene-decanoate)-, poly(octylene-adipate). Examples of polyamides include poly(ethylene-adipamide), poly(propylene-adipamide), poly(butylenes-adipamide), poly(pentylene-adipamide), poly(hexylene-adipamide), poly(octylene-adipamide), poly(ethylene-succinimide), and poly(propylene-sebecamide). Examples of polyimides include poly(ethylene-adipimide), poly(propylene-adipimide), poly(butylene-adipimide), poly(pentylene-adipimide), poly(hexylene-adipimide), poly(octylene-adipimide), poly(ethylene-succinimide), poly(propylene-succinimide), and poly(butylene-succinimide).

The crystalline resin may be present, for example, in an amount of from about 1 to about 50 percent by weight of the components, such as from about 3 percent to about 40 percent by weight of the components, or from about 5 to about 35 percent by weight of the components. The crystalline resin can possess various melting points of, for example, from about 30° C. to about 120° C., such as from about 40° C. to about 100° C., or from about 50° C. to about 90° C. The crystalline resin may have a number average molecular weight ($M_N$), as measured by gel permeation chromatography (GPC) of, for example, from about 1,000 to about 50,000, such as from about 1,500 to about 40,000, or from about 2,000 to about 25,000, and a weight average molecular weight ($M_W$) of, for example, from about 2,000 to about 100,000, such as from about 1,500 to about 90,000, or from about 3,000 to about 80,000, as determined by Gel Permeation Chromatography using polystyrene standards. The polydispersity index ($M_W/M_N$) of the crystalline resin may be any desired value, such as, for example, a polydispersity index of from about 2 to about 6, such as from about 3 to about 4.

Examples of diacids or diesters including vinyl diacids or vinyl diesters utilized for the preparation of amorphous polyesters include dicarboxylic acids or diesters such as terephthalic acid, phthalic acid, isophthalic acid, fumaric acid, trimellitic acid, dimethyl fumarate, dimethyl itaconate, cis, 1,4-diacetoxy-2-butene, diethyl fumarate, diethyl maleate, maleic acid, succinic acid, itaconic acid, succinic acid, succinic anhydride, dodecylsuccinic acid, dodecylsuccinic anhydride, glutaric acid, glutaric anhydride, adipic acid, pimelic acid, suberic acid, azelaic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and combinations thereof. The organic diacids or diesters may be present, for example, in an amount from about 40 to about 60 mol % of the resin, such as from about 42 to about 52 mol % of the resin, or from about 45 to about 50 mol % of the resin.

Examples of diols which may be utilized in generating the amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hydroxyethyl)-bisphenol A, bis(2-hydroxypropyl)-bisphenol A, 1,4-cyclohexanedimethanol, 1,3-cyclohexanedimethanol, xylenedimethanol, cyclohexanediol, diethylene glycol, bis(2-hydroxyethyl)oxide, dipropylene glycol, dibutylene, and combinations thereof. The amount of organic diols selected can vary, and may be present, for example, in an amount from about 40 to about 60 mol % of the resin, such as from about 42 to about 55 mol % of the resin, or from about 45 to about 53 mol % of the resin.

Polycondensation catalysts which may be utilized in forming either the crystalline or amorphous polyesters include tetraalkyl titanates, dialkyltin oxides such as dibutyltin oxide, tetraalkyltins such as dibutyltin dilaurate, and dialkyltin oxide hydroxides such as butyltin oxide hydroxide, aluminum alkoxides, alkyl zinc, dialkyl zinc, zinc oxide, stannous oxide, or combinations thereof. Such catalysts may be utilized in amounts of, for example, from about 0.01 to about 5 mol %, or from about 0.1 to about 4.5 mol %, or from about 0.5 to about 4 mol %, based on the starting diacid or diester used to generate the polyester resin.

In embodiments, as noted above, an unsaturated amorphous polyester resin may be utilized as a latex resin. Examples of such resins include those disclosed in U.S. Pat. No. 6,063,827, the disclosure of which is hereby incorporated by reference in its entirety. Exemplary unsaturated amorphous polyester resins include poly(propoxylated bisphenol co-fumarate), poly(ethoxylated bisphenol co-fumarate), poly(butyloxylated bisphenol co-fumarate), poly(co-propoxylated bisphenol co-ethoxylated bisphenol co-fumarate), poly(1,2-propylene fumarate), poly(propoxylated bisphenol co-maleate), poly(ethoxylated bisphenol co-maleate), poly(butyloxylated bisphenol co-maleate), poly(co-propoxylated bisphenol co-ethoxylated bisphenol co-maleate), poly(1,2-propylene maleate), poly(propoxylated bisphenol co-itaconate), poly(ethoxylated bisphenol co-itaconate), poly(butyloxylated bisphenol co-itaconate), poly(co-propoxylated bisphenol co-ethoxylated bisphenol co-itaconate), poly(1,2-propylene itaconate), and combinations thereof.

In embodiments, a suitable amorphous polyester resin may be a poly(propoxylated bisphenol A co-fumarate) resin having the following formula:

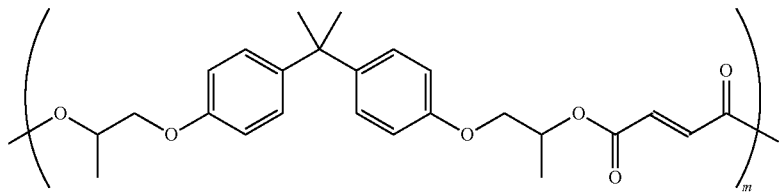

wherein m may be from about 5 to about 1000, such as from about 7 to about 750, or from about 10 to about 500. Examples of such resins and processes for their production may include those disclosed in U.S. Pat. No. 6,063,827, the disclosure of which is hereby incorporated by reference in its entirety.

An example of a linear propoxylated bisphenol A fumarate resin which may be utilized as a latex resin is available under the trade name SPAM from Resana SIA Industrias Quimicas, Sao Paulo Brazil. Other propoxylated bisphenol A fumarate resins that may be utilized and are commercially available include GTUF and FPESL-2 from Kao Corporation, Japan, and EM181635 from Reichhold, Research Triangle Park, N.C., and the like.

Suitable crystalline resins may include those disclosed in U.S. Patent Application Publication No. 2006/0222991, the disclosure of which is hereby incorporated by reference in its entirety. In embodiments, a suitable crystalline resin may be composed of ethylene glycol and a mixture of dodecanedioic acid and fumaric acid co-monomers with the following formula:

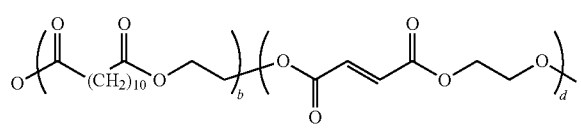

wherein b may be from about 5 to about 2000, such as from about 7 to about 1750, or from about 10 to about 1500; and d may be from about 5 to about 2000, such as from about 7 to about 1750, or from about 10 to about 1500.

The amorphous resin may be present, for example, in an amount of from about 30 to about 90 percent by weight of the components, such as from about 35 to about 85 percent by weight of the components, or from about 40 to about 80 percent by weight of the components. In embodiments, the amorphous resin or combination of amorphous resins utilized in the latex may have a glass transition temperature of from about 30° C. to about 80° C., such as from about 33° C. to about 85° C., or from about 35° C. to about 70° C. In further embodiments, the combined resins utilized in the latex may have a melt viscosity of from about 10 to about 1,000,000 PaS at about 130° C., such as from about 25 to about 500,000, or from about 50 to about 100,000 PaS.

One, two, or more resins may be used. In embodiments, where two or more resins are used, the resins may be in any suitable ratio (e.g., weight ratio) such as for instance of from about 1% (first resin)/99% (second resin) to about 99% (first resin)/1% (second resin), such as from about 10% (first resin)/90% (second resin) to about 90% (first resin)/10% (second resin). Where the resin includes an amorphous resin and a crystalline resin, the weight ratio of the two resins may be from about 99% (amorphous resin):1% (crystalline resin), to about 1% (amorphous resin):90% (crystalline resin).

In embodiments the resin may possess acid groups which, in embodiments, may be present at the terminal of the resin. Acid groups which may be present include carboxylic acid groups, and the like. The number of carboxylic acid groups may be controlled by adjusting the materials utilized to form the resin and reaction conditions.

In embodiments, the resin may be a polyester resin having an acid number from about 2 mg KOH/g of resin to about 200 mg KOH/g of resin, in embodiments from about 5 mg KOH/g of resin to about 50 mg KOH/g of resin. The acid containing resin may be dissolved in tetrahydrofuran solution. The acid number may be detected by titration with KOH/methanol solution containing phenolphthalein as the indicator. The acid number may then be calculated based on the equivalent amount of KOH/methanol required to neutralize all the acid groups on the resin identified as the end point of the titration.

Neutralizing Agent

In embodiments, the resin may be pre-blended with a weak base or neutralizing agent. In embodiments the base may be a solid, which avoids the risks and difficulties associated with pumping of a solution.

In embodiments, the resin and the neutralizing agent may be simultaneously fed through a co-feeding process, which may accurately control the feed rate of both the base and the resin into the extruder throughout the process. Utilizing this process allows for control of the base concentration and a more efficient process. Co-feeding may allow for process repeatability and stability, and significantly lower initial start-up waste.

In embodiments, the neutralizing agent may be used to neutralize acid groups in the resins, so a neutralizing agent herein may also be referred to as a "basic neutralization agent." Any suitable basic neutralization reagent may be used in accordance with the present disclosure. In embodiments, suitable basic neutralization agents may include both inorganic basic neutralization agents and organic basic neutralization agents. Suitable basic neutralization agents may include ammonium hydroxide, potassium hydroxide, sodium hydroxide, sodium carbonate, sodium bicarbonate, lithium hydroxide, potassium carbonate, combinations thereof, and the like. Suitable basic neutralization agents may also include monocyclic compounds and polycyclic compounds having at least one nitrogen atom, such as, for example, secondary amines, which include aziridines, azetidines, piperazines, piperidines, pyridines, bipyridines, terpyridines, dihydropyridines, morpholines, N-alkylmorpholines, 1,4-diazabicyclo[2.2.2]octanes, 1,8-diazabicycloundecanes, 1,8-diazabicycloundecenes, dimethylated pentylamines, trimethylated pentylamines, pyrimidines, pyrroles, pyrrolidines, pyrrolidinones, indoles, indolines, indanones, benzindazones, imidazoles, benzimidazoles, imidazolones, imidazolines, oxazoles, isoxazoles, oxazolines, oxadiazoles, thiadiazoles, carbazoles, quinolines, isoquinolines, naphthyridines, triazines, triazoles, tetrazoles, pyrazoles, pyrazolines, and combinations thereof. In embodiments, the monocyclic and polycyclic compounds may be unsubstituted or substituted at any carbon position on the ring. Monocyclic and polycyclic compounds may be substituted by replacing hydrogen atoms with one or more functional groups to form monocyclic and polycyclic derivative compounds. The term "functional group" refers, for example, to a group of atoms arranged in a way that determines the chemical properties of the group and the molecule to which it is attached. Examples of functional groups include halogen atoms, hydroxyl groups, carboxylic acid groups, and the like. The term "derivative" refers, for example, to a compound derived from another.

The basic neutralization agent may be utilized as a solid such as, for example, sodium hydroxide powder, so that it is present in an amount of from about 0.001% by weight to about 50% by weight of the resin, such as from about 0.01% by weight to about 25% by weight of the resin, or from about 0.1% by weight to about 5% by weight of the resin.

As noted above, the basic neutralization agent may be added to a resin possessing acid groups. The addition of the basic neutralization agent may thus raise the pH of an emulsion including a resin possessing acid groups from about 5 to about 12, such as from about 6 to about 11, or from about 5 to about 10. The neutralization of the acid groups may, in embodiments, enhance formation of the emulsion.

Surfactants

In embodiments, the process of the present disclosure includes adding a surfactant during extrusion of the resin. Where utilized, a resin emulsion may include one, two, or more surfactants. The surfactants may be selected from ionic surfactants and nonionic surfactants. Anionic surfactants and cationic surfactants are encompassed by the term "ionic surfactants." In embodiments, the surfactant may be added as a solution, such as an aqueous solution, with a concentration from about 5% to about 100% (pure surfactant) by weight, or from about 30% to about 95% by weight. In embodiments, the surfactant may be utilized so that it is present in an amount of from about 0.01% to about 20% by weight of the resin, such as from about 0.1% to about 10% by weight of the resin, or from about 1% to about 8% by weight of the resin.

Examples of nonionic surfactants that can be utilized for the processes illustrated herein and that may be included in the emulsion are, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, available from Rhone-Poulenc as IGEPAL CA210™, IGEPAL CA520™, IGEPAL CA720™, IGEPAL CO-890™, IGEPAL CO-720™, IGEPAL CO-290™, IGEPAL CA210™, ANTAROX 890™ and ANTAROX 897™. Other examples of suitable nonionic surfactants include a block copolymer of polyethylene oxide and polypropylene oxide, including those commercially available as SYNPERONIC PE/F, in embodiments SYNPERONIC PE/F 108.

Anionic surfactants which may be utilized include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ obtained from Daiichi Kogyo Seiyaku, combinations thereof, and the like. Other suitable anionic surfactants include, in embodiments, DOWFAX™ 2A1, an alkyldiphenyloxide disulfonate from The Dow Chemical Company, and/or TAYCA POWER BN2060 from Tayca Corporation (Japan), which are branched sodium dodecyl benzene sulfonates. Combinations of these surfactants and any of the foregoing anionic surfactants may be utilized in embodiments.

Examples of the cationic surfactants, which are usually positively charged, include, for example, alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, MIRAPOL™ and ALKAQUAT™, available from Alkaril Chemical Company, SANIZOL™ (benzalkonium chloride), available from Kao Chemicals, and the like, and mixtures thereof.

EXAMPLES

Example 1

Figure 2A:
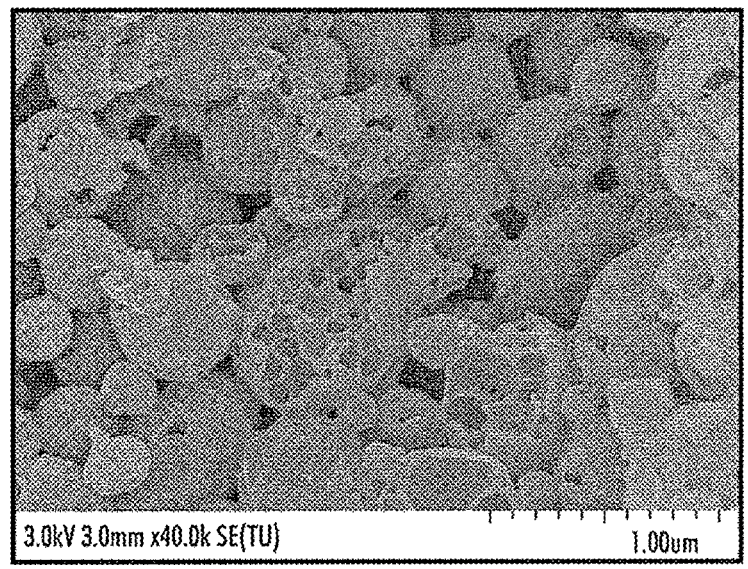
FIG. 2A is an SEM image of the porous nanoparticles produced in Example 1 at ×40.0 k magnification.
Figure 2B:
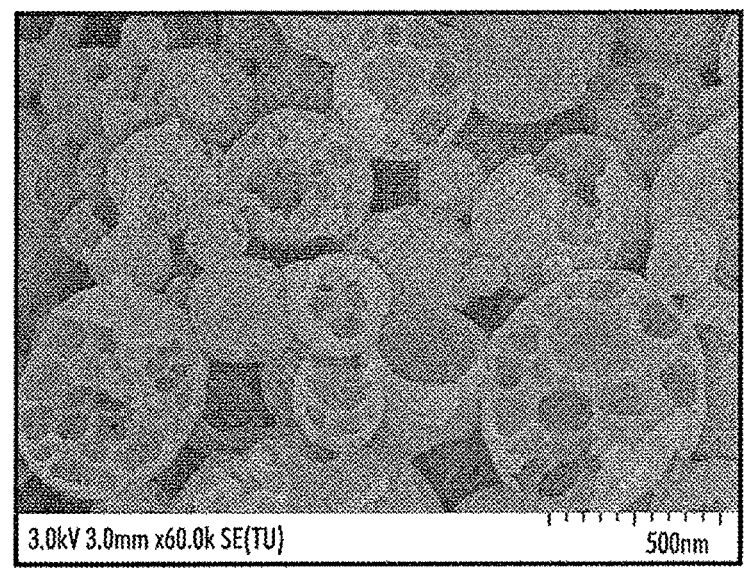
FIG. 2B is an SEM image of the porous nanoparticles produced in Example 1 at ×60 k magnification.

Preparation of a Sub-Micron Sized Latex Emulsion with Nanoporous Morphology Formed from an Amorphous Polyester Resin 100 parts of an amorphous polyester resin were blended with 1 part sodium hydroxide powder. The mixture was added to the hopper of a gravimetric feeder and fed at a rate of 1.25 kg/hour to the feeding throat in zone 0 of a twin-screw extruder having seven heated zones plus a heated die for a total of eight heated zones and one cooled feeding zone. The temperatures of the eight heated zones of the twin-screw extruder are summarized in Table 1. The screw speed of the extruder was set to 300 RPM. In zone 2 of the screw extruder, an aqueous surfactant solution comprising 47% DOWFAX 2A1 was injected at a rate of 2.89 mL/min. In zone 3 of the twin-screw extruder, deionized water was injected at a rate of 4.44 mL/min. In zone 6 of the twin-screw extruder, deionized water was injected at a rate of 24.97 mL/min. Porous nanoparticles were collected after being discharged from the extruder. The process conditions of Example 1 are summarized in Table 1. SEM images of a representative sample of the porous nanoparticles produced in Example 1 are shown in FIG. 2A (at ×40.0 k magnification) and FIG. 2B (at ×60 k magnification).

Example 2

Figure 3A:
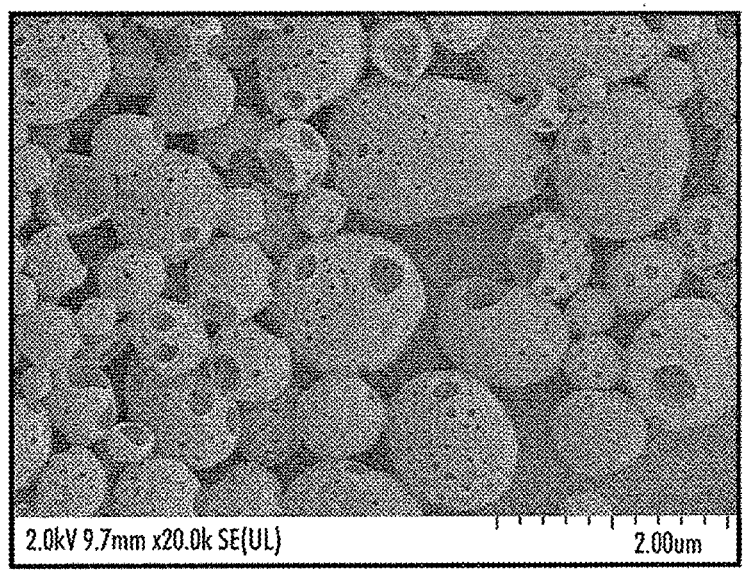
FIG. 3A is an SEM image of the porous nanoparticles produced in Example 2 at ×20.0 k magnification.

Preparation of a Sub-Micron Sized Latex Emulsion with Nanoporous Morphology 100 parts of an amorphous polyester resin were blended with 1 part sodium hydroxide powder. The mixture was added to the hopper of a gravimetric feeder and fed at a rate of 1.25 kg/hr to the feeding throat in zone 0 of a twin-screw extruder having seven heated zones plus a heated die for a total of eight heated zones and one cooled feeding zone. The temperatures of the eight heated zones of the twin-screw extruder are summarized in Table 1. The screw speed of the extruder was set to 300 RPM. In zone 2 of the twin-screw extruder, an aqueous surfactant solution comprising 47% DOWFAX 2A1 was injected at a rate of 2.89 mL/min. In zone 3 of the twin-screw extruder, deionized water was injected at a rate of 6.51 mL/min. In zone 6 of the twin-screw extruder, deionized water was injected at a rate of 50.00 mL/min. Porous nanoparticles were collected after being discharged from the extruder. The process conditions of Example 2 are summarized in Table 1. SEM images of a representative sample of the porous nanoparticles produced in Example 2 are shown in FIG. 3A (at ×20 k magnification) and FIG. 3B (at ×10.0 k magnification).

Figure 3B:
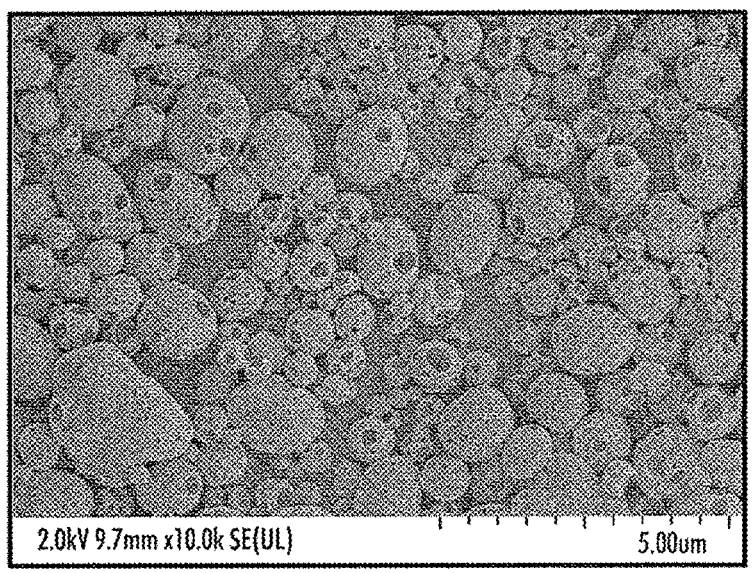
FIG. 3B is an SEM image of the porous nanoparticles produced in Example 2 at ×10.0 k magnification.

As discussed above, the morphology of the porous nanoparticles may be controlled by adjusting the injection rate of the second aqueous solution comprising deionized water. For example, of a representative sample of such porous nanoparticles are shown in FIG. 3A and FIG. 3B, where the surface porosity was created (in a process similar to that employed in Example 2) by increasing the injection rate of the second aqueous solution comprising deionized water at N1 (see FIG. 1).

TABLE 1

Example 2 process conditions.

| Example | Resin (1 ppH NaOH) | Surfactant [N0] | $Z_3$ DIW [N1] | $Z_6$ DIW [N2] | RPM | Z1 | Z2 | Z3 | Z4 | Z5 | Z6 | Z7 | Z8 |
|---|---|---|---|---|---|---|---|---|---|---|---|---|---|
| 1 | 1.25 kg/h | 2.89 mL/min | 4.44 mL/min | 24.97 mL/min | 300 | 160 | 170 | 150 | 130 | 110 | 110 | 90 | 90 |
| 2 | 1.25 kg/h | 2.89 mL/min | 6.51 mL/min | 50.00 mL/min | 300 | 160 | 170 | 150 | 130 | 110 | 100 | 90 | 90 |

Example 3

Figure 4A:
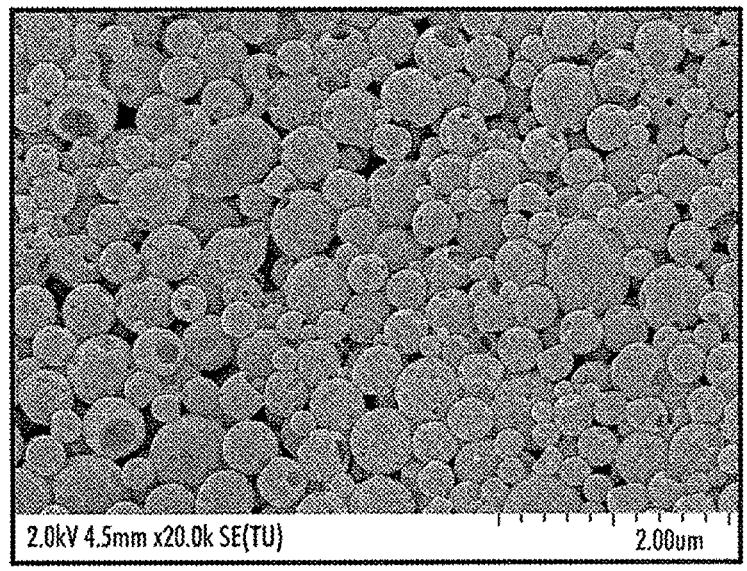
FIG. 4A is an SEM image of the porous nanoparticles produced in Example 3 at ×20.0 k magnification.
Figure 4B:
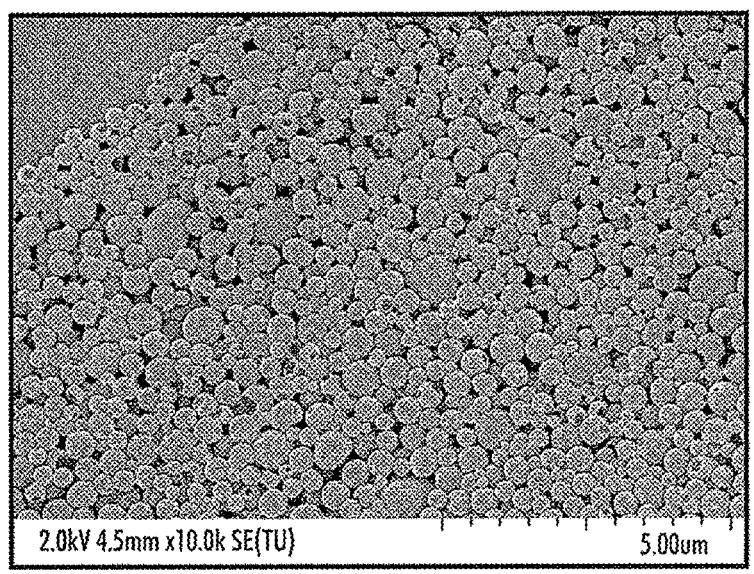
FIG. 4B is an SEM image of the porous nanoparticles produced in Example 3 at ×10.0 k magnification.

Preparation of a Sub-Micron Sized Latex Emulsion with Nanoporous Morphology Formed from an Amorphous Polyester Resin 100 parts of an amorphous polyester resin were blended with 1 part sodium hydroxide powder. The mixture was added to the hopper of a gravimetric feeder and fed at a rate of 1.25 kg/hour to the feeding throat in zone 0 of a twin-screw extruder having seven heated zones plus a heated die for a total of eight heated zones and one cooled feeding zone. The temperatures of the eight heated zones of the twin-screw extruder are summarized in Table 2. The screw speed of the extruder was set to 200 RPM. In zone 2 of the screw extruder, an aqueous surfactant solution comprising 21% DOWFAX 2A1 was injected at a rate of 6 mL/min. In zone 3 of the twin-screw extruder, an aqueous surfactant solution comprising 21% DOWFAX 2A1 was injected at a rate of 3 mL/min. In zone 6 of the twin-screw extruder, deionized water was injected at a rate of 38.43 mL/min. Porous nanoparticles were collected after being discharged from the extruder. The process conditions of Example 3 are summarized in Table 2. SEM images of a representative sample of the porous nanoparticles produced in Example 3 are shown in FIG. 4A (at ×20 k magnification) and FIG. 4B (at ×10.0 k magnification).

Example 4

Figure 5A:
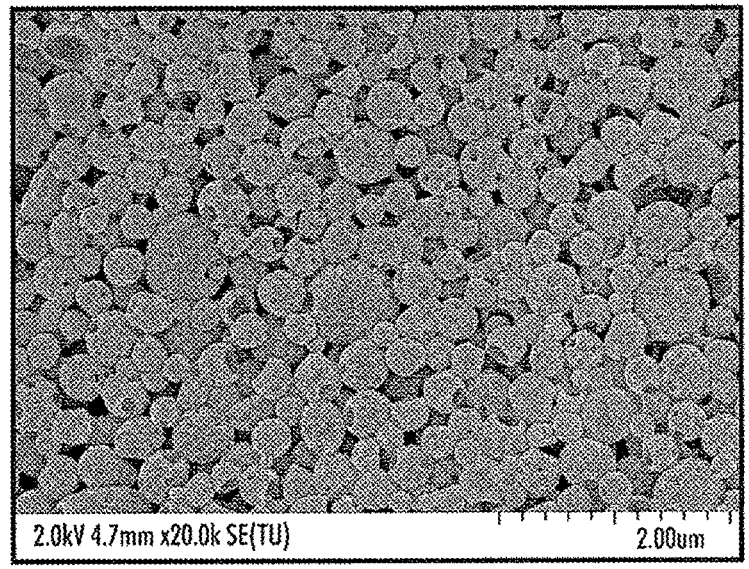
FIG. 5A is an SEM image of the porous nanoparticles produced in Example 4 at ×20.0 k magnification.
Figure 5B:
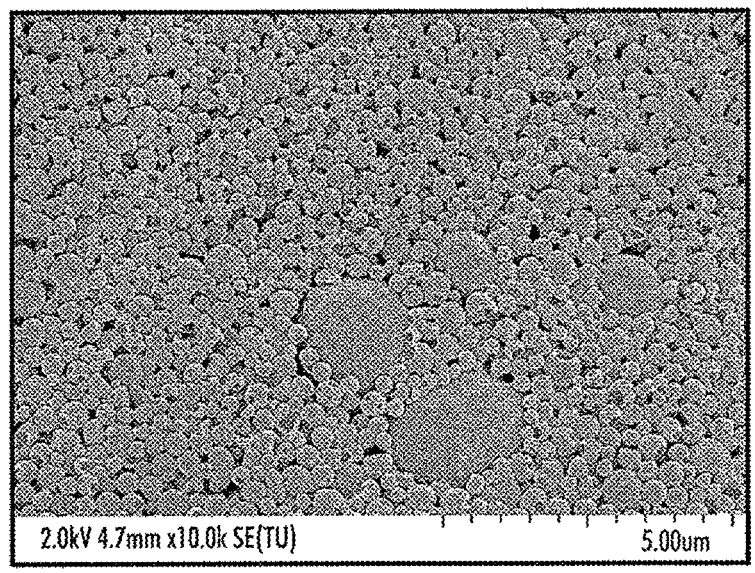
FIG. 5B is an SEM image of the porous nanoparticles produced in Example 4 at ×10.0 k magnification.

Preparation of a Sub-Micron Sized Latex Emulsion with Nanoporous Morphology Formed from an Amorphous Polyester Resin 100 parts of an amorphous polyester resin were blended with 1 part sodium hydroxide powder. The mixture was added to the hopper of a gravimetric feeder and fed at a rate of 1.25 kg/hour to the feeding throat in zone 0 of a twin-screw extruder having seven heated zones plus a heated die for a total of eight heated zones and one cooled feeding zone. The temperatures of the eight heated zones of the twin-screw extruder are summarized in Table 2. The screw speed of the extruder was set to 200 RPM. In zone 2 of the screw extruder, an aqueous surfactant solution comprising 21% DOWFAX 2A1 was injected at a rate of 8 mL/min. In zone 3 of the twin-screw extruder, an aqueous surfactant solution comprising 21% DOWFAX 2A1 was injected at a rate of 1 mL/min. In zone 6 of the twin-screw extruder, deionized water was injected at a rate of 38.43 mL/min. Porous nanoparticles were collected after being discharged from the extruder. The process conditions of Example 4 are summarized in Table 2. SEM images of a representative sample of the porous nanoparticles produced in Example 4 are shown in FIG. 5A (at ×20 k magnification) and FIG. 5B (at ×10 k magnification).

TABLE 2

Example 4 process conditions.

| Example | Resin (1 ppH NaOH) | $Z_2$ 21% DOWFAX 2A1 [N0] | $Z_3$ 21% DOWFAX 2A1 [N1] | $Z_6$ DIW [N2] | RPM | Zone Temperature (° C.) | | | | | | | |
|---|---|---|---|---|---|---|---|---|---|---|---|---|---|
| | | | | | | Z1 | Z2 | Z3 | Z4 | Z5 | Z6 | Z7 | Z8 |
| 3 | 1.25 kg/h | 6 mL/min | 3 mL/min | 38.43 | 200 | 160 | 165 | 135 | 115 | 95 | 95 | 95 | 125 |
| 4 | 1.25 kg/h | 8 mL/min | 1 mL/min | 38.43 | 200 | 160 | 165 | 135 | 115 | 95 | 95 | 95 | 125 |

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A process for producing porous nanoparticles, the process comprising:
    continuously adding a resin composition comprising at least one resin to a feed section of a screw extruder, wherein the screw extruder is segmented and at least one of the segments is heated to a temperature of from 70° C. to 200° C.;
    adding a first aqueous solution comprising a surfactant to the resin composition to form a water-in-oil emulsion in the screw extruder which results in the surfactant within the resin;
    adding a second aqueous solution comprising deionized water to the water-in-oil emulsion in the screw extruder to form a water-in-oil-in-water double emulsion comprising porous nanoparticles having cell walls with a cell wall thickness in the range of from about 10 nm to about 50 nm; and
    recovering porous nanoparticles from the double emulsion in the screw extruder;
    wherein the porous nanoparticles have a particle size of from about 50 nm to about 2 μm and a pore diameter of from about 20 nm to about 400 nm;
    wherein each of the solutions and the composition utilized during the process of forming the porous nanoparticles are substantially free of organic solvents.

2. The process according to claim 1, wherein the resin composition further comprises a neutralizing agent.

3. The process according to claim 2, wherein the neutralizing agent is sodium hydroxide.

4. The process according to claim 1, further comprising adding deionized water after formation of the double emulsion.

5. The process according to claim 1, wherein the porous nanoparticles recovered from the double emulsion comprise at least one member selected from the group consisting of an active compound, a cosmetic compound, and a pharmaceutical compound.

6. The process according to claim 1, wherein the first aqueous solution comprising a surfactant further comprises at least one member selected from the group consisting of an active compound, a cosmetic compound, and a pharmaceutical compound.

7. The process according to claim 1, wherein the second aqueous solution further comprises a surfactant.

8. The process according to claim 1, wherein the at least one resin is a polyester resin selected from the group consisting of amorphous resins, crystalline resins, and combinations thereof.

9. The process according to claim 1, wherein the at least one resin comprises an amorphous polyester resin.

* * * * *